US005726404A

United States Patent [19]

Brody

[11] Patent Number: 5,726,404
[45] Date of Patent: Mar. 10, 1998

[54] VALVELESS LIQUID MICROSWITCH

[75] Inventor: James P. Brody, Seattle, Wash.

[73] Assignee: University of Washington, Seattle, Wash.

[21] Appl. No.: 656,155

[22] Filed: May 31, 1996

[51] Int. Cl.$^6$ ............ G05D 7/01; B01D 15/08; G01N 33/543; G01N 33/558
[52] U.S. Cl. .......... 200/81 R; 137/261; 137/262; 137/391; 204/299 R; 435/7.2; 422/50
[58] Field of Search ............ 200/81 R; 137/261, 137/262, 391, 487, 504; 204/299 R; 250/461.2; 73/861.04; 210/198.2, 657; 60/204; 435/7.2; 422/6, 55, 58, 50, 61, 259, 287.2, 288.5

[56] References Cited

U.S. PATENT DOCUMENTS

| 4,000,754 | 1/1977 | Risk ............ 137/487 |
| 4,908,112 | 3/1990 | Pace ............ 204/299 R |
| 5,097,863 | 3/1992 | McCann et al. ............ 137/504 |
| 5,587,128 | 12/1996 | Wilding et al. ............ 422/50 |
| 5,589,642 | 12/1996 | Agar et al. ............ 73/861.04 |
| 5,593,838 | 1/1997 | Zanzucchi et al. ............ 435/6 |
| 5,595,650 | 1/1997 | Manz ............ 210/198.2 |
| 5,599,503 | 2/1997 | Manz et al. ............ 422/82.05 |
| 5,635,358 | 6/1997 | Wilding et al. ............ 435/7.2 |
| 5,636,513 | 6/1997 | Pahl ............ 60/204 |

OTHER PUBLICATIONS

Brody, J.P and Yager, P., "Low Reynolds Number Micro-Fluidic Devices," Solid-State Sensor and Actuator Workshop, Hilton Head, SC (Jun. 1996) pp. 105–108.
Ramsey, J.M. et al., "Microfabricated chemical measurement systems," NATURE Medicine (Oct. 1995) 1(10):1093–1096.
Elwenspoek, M. et al., "Towards integrated microliquid handling systems," J. Micromech. Microeng. (1994) 4:227–243.
Shoji, S. and Esashi, M., "Microflow devices and systems," J. Micromech. Microeng. (1994) 4:157–171.
Verpoorte, E.M.J. et al., "Three-dimensional micro flow manifolds for miniaturized chemical analysis sytems," J. Micromech. Microeng. (1994) 4:246–256.
Vollmer, J. et al., "Bistable fluidic elements in LIGA technique for flow control in fluidic microactuators," Sensors and Actuators A (1994) 43:330–334.
Wilding, P. et al., "Manipulation and Flow of Biological Fluids in Straight Channels Micromachined in Silicon," Clin. Chem. (1994) 40(1):43–47.
Gravesen, P. et al., "Microfluidics—a review," J. Micromech. Microeng. (1993) 3:168–182.
Manz, A. et al., "Planar Chips Technology for Miniaturization of Separation systems: A Developing Perspective in Chemical Monitoring," Advances in Chromatography (1993) 33:1–66.
Moroney, R.M. et al., "Microtransport induced by ultrasonic Lamb waves," Appl. Phys. Lett (1991) 59(7):774–776.

*Primary Examiner*—Adolf Berhane
*Assistant Examiner*—Rajnikani B. Patel
*Attorney, Agent, or Firm*—Greenlee, Winner & Sullivan, P.C.

[57] ABSTRACT

This invention provides a valveless method and apparatus for high speed switching of liquid flow between intersecting microchannels. Liquid flow is controlled by manipulating external driving pressures. The switch comprises three intersecting microchannels, each having a liquid reservoir at its nonintersecting end for liquid inlet and outlet. It further includes applying a driving pressure to each reservoir switching the driving pressures. The microswitch of this invention operates to establish a liquid flow from a first channel to a second channel by applying a pressure differential between the first and second reservoirs, while simultaneously preventing flow into the third channel by applying a pressure to the third reservoir which equals the pressure at the junction of the three channels. By switching one or more driving pressures, the flow to the second channel can be stopped and the liquid flow redirected to the third channel. This invention further includes switches wherein more than three channels are included in the flow network, either intersecting in a single junction or in multiple junctions.

39 Claims, 7 Drawing Sheets

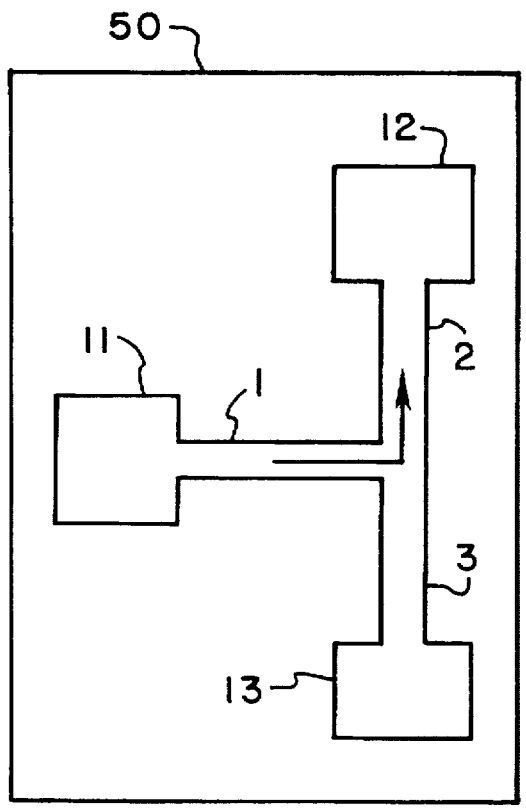
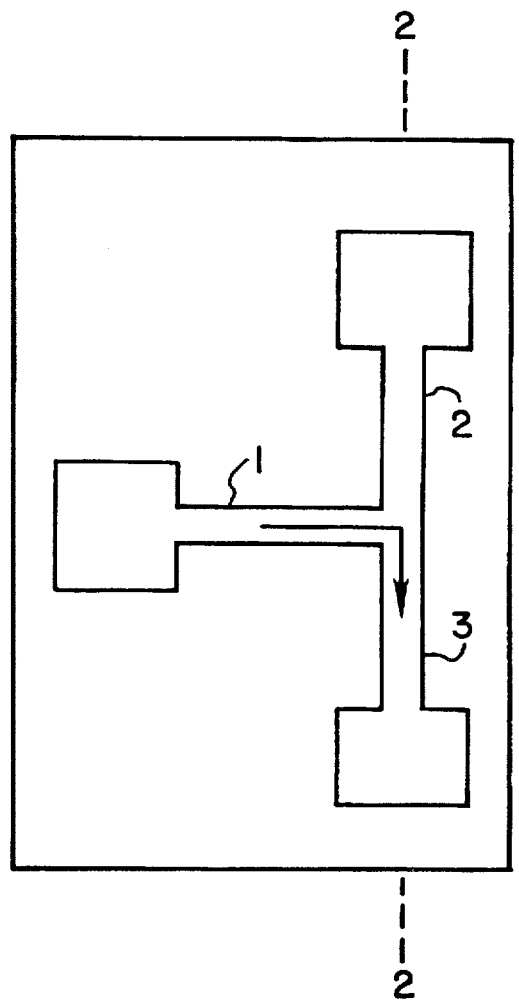
Fig. 1a            Fig. 1b
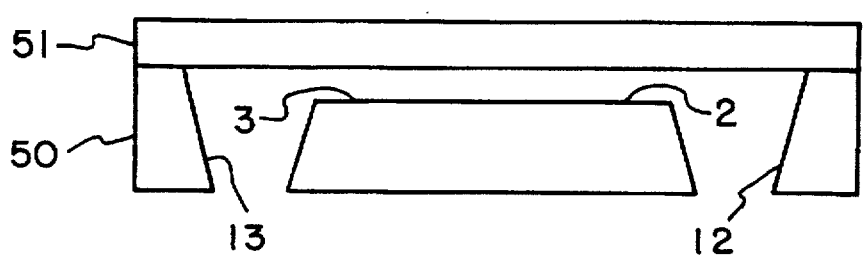
Fig. 2

5,726,404

VALVELESS LIQUID MICROSWITCH

This invention was made with Government support under contract DAMD17-94-J-4460 awarded by the U.S. Army. The Government has certain rights in the invention.

FIELD OF THE INVENTION

This invention relates to switching between flow channels in integrated microfluid handling systems manifolds.

BACKGROUND OF THE INVENTION

Integrated microfluid handling systems that provide control over nanoliter sized volumes of liquid will be extraordinarily useful in both miniaturizing present analytical tests and handling the small sample sizes frequently used in biomedical testing. The goal is to perform the entire chemical analysis in a single micromachined device, from preliminary treatment of the sample, to mixing of reagents, separation of the analyte of interest, measurement of the analyte, and further mixing, separation and measurement stages. Among the micromachined components required are channels, valves, pumps, flow sensors, mixing chambers and optical detectors.

In a flow manifold having branching or joining flow channels, it may be necessary to switch the flow route from one channel to another. Numerous microvalves having integral moving parts have been described (see, for example, Shoji et al., J. Micromech Microeng. 4 (1994), 157-171). They were initially developed for gaseous fluids but some have now been used for liquids as well. The moving part can be, for example, a valve cap which seals against a valve seat, a cantilever closure plate or a membrane. Valve parts can be actively moved using solenoid, piezoelectric, shape memory alloy, electrostatic, pneumatic, electromagnetic or bimetallic actuators. There are also passive microvalves which allow flow in one direction but close in response to flow in the reverse direction. Disadvantages of valves utilizing moving parts include the complexity and expense of fabrication, and the fragility of the components.

Electrokinetic pumping can direct fluid flow within microchannels without the use of integral moving parts (see, for example, Manz et al., Advances in Chromatography 33 (1993), 1-67). Each capillary in the manifold network is connected to a liquid reservoir, and voltages are applied to electrodes in the liquid reservoirs to create an electric field which drives the liquid by electroosmotic and electrophoretic propulsion. Flow routes within the manifold are controlled by the applied fields. Electrokinetic pumping requires high applied voltages, typically in the kV range, and can only be performed in nonconducting channels. While planar glass devices are well suited, the switch cannot be fabricated on silicon wafers unless an insulating layer is added. Such layers are subject to breakdown under high fields.

Wall attachment fluid switches have been used to construct fluid logic circuits on a macroscale. Each switch, also termed a fluid amplifier, has a fluid input channel and two output channels. Due to a low pressure bubble created by the bending of the fluid jet toward one output channel, the jet attaches itself to that channel wall. A control channel intersects each output channel near the junction of the channels. By temporary application of a control pressure at one control port, the wall attachment is interrupted and the fluid flow is switched to the opposite output channel. Recently, a wall attachment amplifier has been demonstrated on a microscale (Vollmer et al., Sensors and Actuators 43 (1994), 330-334). The fluid which has been switched by wall attachment amplifiers is gaseous; the wall attachment effect cannot be used with liquids on a microscale because the Reynolds number is too low.

SUMMARY OF THE INVENTION

This invention provides a valveless method and apparatus for high speed switching of liquid flow between intersecting microchannels. Liquid flow is controlled by manipulating external driving pressures. The switch is simple to fabricate, has no integral moving parts, does not require high voltages, and can be fabricated in a silicon wafer. The switch operates in the low Reynolds number regime where fluid dynamics are dominated by viscous forces rather than inertial forces. Because of this, the microswitch of the present invention is inherently different from macroscopic devices.

The switch comprises three intersecting microchannels, each having a liquid reservoir at its nonintersecting end for liquid inlet and outlet. It further includes a means for applying a driving pressure to each reservoir and a means for switching the driving pressures. For a liquid flow channel having a higher pressure at one end than the other, there is a pressure gradient along the channel and the pressure at any point depends on the distance along the channel. The microswitch of this invention operates to establish a liquid flow from a first channel to a second channel by applying a pressure differential between the first and second reservoirs, while simultaneously preventing flow into the third channel by applying a pressure to the third reservoir which equals the pressure at the junction of the three channels. By switching one or more driving pressures, the flow to the second channel can be stopped and the liquid flow redirected to the third channel. The switch can also be operated in reverse, whereby liquid from either the first or second channel can be selected to flow into the third channel.

This invention further includes switches wherein more than three channels are included in the flow network, either intersecting in a single junction or in multiple junctions. These can be used for selecting between more than two samples or reagents to introduce to the manifold, for separating the sample into more than two destinations, or for both mixing and separating liquids.

Silicon or other micromachinable material can be used to fabricate the switch. In the preferred embodiment, channels are etched in the front surface of a wafer and ports are etched through the wafer to the backside for fluid connection. A cover plate is bonded to the front surface to seal the flow channels. Pressure is applied behind the ports using a compressed gas cylinder with a regulator and valve to control and switch the pressures.

BRIEF DESCRIPTION OF THE DRAWING

FIG. 1, comprising FIGS. 1a–b, is a plan view of the microchannels of the microswitch showing liquid flow switching between a first and a second output channel.

FIG. 2 is a cross section of the microchannels.

FIG. 3, comprising

FIG. 7, comprising

DETAILED DESCRIPTION OF THE INVENTION

Figure 3A:
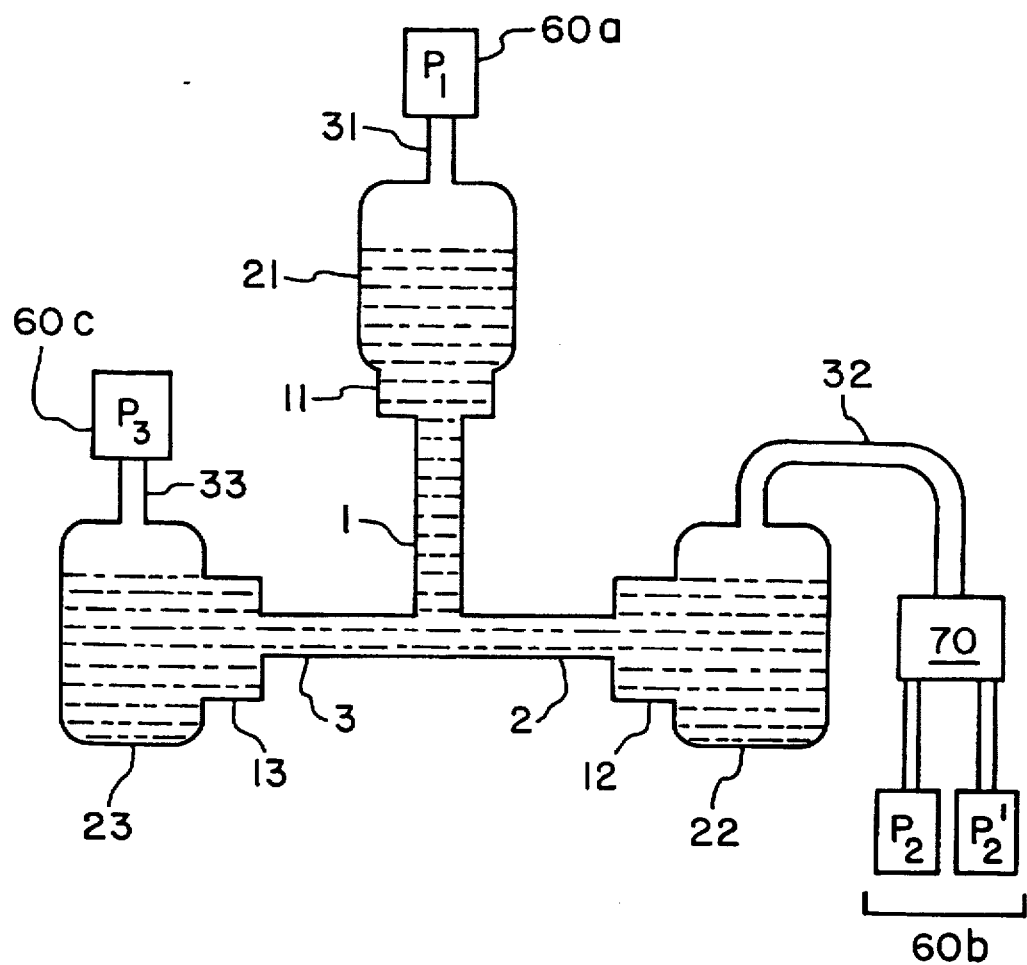
FIGS. 3a–b, is schematic drawings of pressure control and switching means wherein the pressure is switched (a) on a single channel and (b) on two channels simultaneously.

FIGS. 1 and 2 show the microchannels of the microswitch of this invention in plan view and in cross section. In this embodiment channels 1, 2 and 3 are formed in substrate 50 and sealed by coverplate 51. Cover plate 51 can be transparent to allow optical access to the channels. It can contain additional fluidic, optical, electronic or mechanical elements, as can substrate 50. One end of each of channels 1–3, termed herein the junction end, joins with the other channels to form a junction. The other end of each channel, termed herein the port end, is connected to a liquid reservoir (not shown). In this embodiment the connection is made through ports 11, 12 and 13 which are etched through the substrate to connect with liquid reservoirs on the backside. In the illustrated embodiment, liquid enters through channel one and can be switched to exit either through channel two (FIG. 1a) or channel three (FIG. 1b). Alternatively, liquid can enter through channels two and three, and the switch selects which of the inlet liquids flows out through channel one. In another mode of operation liquid flows from channel one to channel two in a first switching state and from channel three to channel one in a second switching state.

Channels one, two and three are microchannels. The term microchannel is used herein for a channel having dimensions which provide low Reynolds number operation, for which fluid dynamics are dominated by viscous forces rather than inertial forces. The ratio inertial forces to viscous forces is $$R = \frac{\rho \left( \frac{\delta u}{\delta t} + (u \cdot \nabla) u \right)}{\eta \nabla^2 u} = \frac{\rho d^2}{\eta \tau} + \frac{\rho u d}{\eta}, \quad (1)$$

where u is the velocity vector, ρ is the fluid density, η is the viscosity of the fluid, d is the characteristic dimension of the channel, and τ is the time scale over which the velocity is changing (where u/τ=δu/δt). The term "characteristic dimension" is used herein for the dimension which determines Reynolds number, as is known in the art. For a cylindrical channel it is the diameter. For a rectangular channel, it depends primarily on the smaller of the width and depth. For a V-shaped channel it depends on the width of the top of the "V".

Fluid flow behavior in the steady state, τ→∞, is characterized by the Reynolds number, $R_e = \rho u r / \eta$. Because of the small sizes and slow velocities, microfabricated fluid systems are often in the low Reynolds number regime ($R_e < 1$). In this regime, inertial effects, which cause turbulence and secondary flows, are negligible; viscous effects dominate the dynamics.

Since the Reynolds number depends not only on channel dimension, but on fluid density, fluid viscosity, fluid velocity and the timescale on which the velocity is changing, the absolute upper limit to the channel diameter is not sharply defined. However, Table 1 gives the switching times and corresponding channel diameters for water using the conservative restriction that R<1. According to Table 1, to achieve switching times <1 s, the characteristic channel dimension should be <1 mm. In fact, with well designed channel geometries, turbulence can be avoided for R<100 and possibly for R<1000, so the actual fastest switching speed and largest characteristic dimension which can be utilized in the switch of the invention are greater than the values in Table 1. The preferred channel characteristic dimension range is between about 0.5 μm and 1 mm. A more preferred range is between about 5 μm and 100 μm.

TABLE 1

| Channel dimension and switching time for R < 1. | |
|---|---|
| Characteristic Dimension | Switching time |
| 1 μm | 1 μs |
| 10 μm | 100 μs |
| 100 μm | 10 ms |
| 1 mm | 1 s |

The channels form a T-shaped junction in the illustrated embodiment. This shape is easily achieved by etching of silicon. The switch operation is described with the stem of the T being a common inlet (or outlet) and the switch selecting which crossbar the liquid flows to (or from). Alternatively one of the crossbars can be the common flow channel. Alternative configurations, such as a Y-shaped junction, can also be used in the microswitch. A Y-shaped junction can be achieved by etching noncrystalline substrates, or in crystalline substrates by isotropic etching, for example reactive ion etching. In the illustrated embodiment the channels diameters are all the same; they can instead by varied. For larger channel diameters, the channels can be made with capillary tubes rather than etched in a substrate.

Liquid reservoirs and a driving pressure system are illustrated schematically in FIG. 3a. Reservoirs 21, 22 and 23 are attached to microchannels 1, 2 and 3 via connection ports 11, 12 and 13. Driving pressures $P_1$, $P_2$, $P_2'$ and $P_3$ are provided by pressure control means 60a–c which supplies pressurized gas to each reservoir via gas inlets 31, 32 and 33. The pressure control means in this embodiment can be a cylinder of pressurized gas, preferably an inert gas, connected to a plurality of pressure regulators. In this embodiment, $P_1$ and $P_3$, are constant but not equal to one another. The pressure behind reservoir 22 is switched between $P_2$ and $P_2'$ by switching means 70. Pressures are designated as $P_n$ in the first switching state and as $P_n'$ in the second state. In this embodiment $P_1 = P_1'$ and $P_3 = P_3'$.

The term liquid reservoir is used herein for any container for providing liquid to an inlet or for receiving liquid from an outlet and via which a pressure can be applied to a microchannel. In the case of an outlet reservoir, the reservoir need not actually collect the liquid but can simply be an outlet from the channel. A reservoir can be an integral part of a substrate containing the microchannels or it can be connected to the substrate. It can have any shape, including channel shaped. When the switch is integrated into a larger system, the other elements of the system that connect to the micro channels, and which input or receive liquids therefrom, constitute the reservoirs of the microswitch. If a microchannel joins two channels in a larger system, and each of the two channels is attached to a reservoir, then the microchannel reservoir comprises both reservoirs. If pressures are applied to both reservoirs, it results in a net driving pressure applied to the microchannel.

The term driving pressure is used herein for a pressure applied to a liquid reservoir. In the illustrated embodiment the pressure control means is regulated pressurized gas. It can alternatively utilize a vacuum pump for providing pressures below atmospheric pressure. Atmospheric pressure can be provided for one of the constant pressures by venting one reservoir to air. Other pressure control means can be used.

The term switching means is used herein for a means for switching one or more driving pressures. In the illustrated switching means, the connection to gas inlet 32 is switched between a first gas supply line at $P_2$ and a second gas supply line at $P_2'$. Alternatively there can be a single gas supply line and the switching means can be a regulator with a switchable output pressure.

Figure 3B:
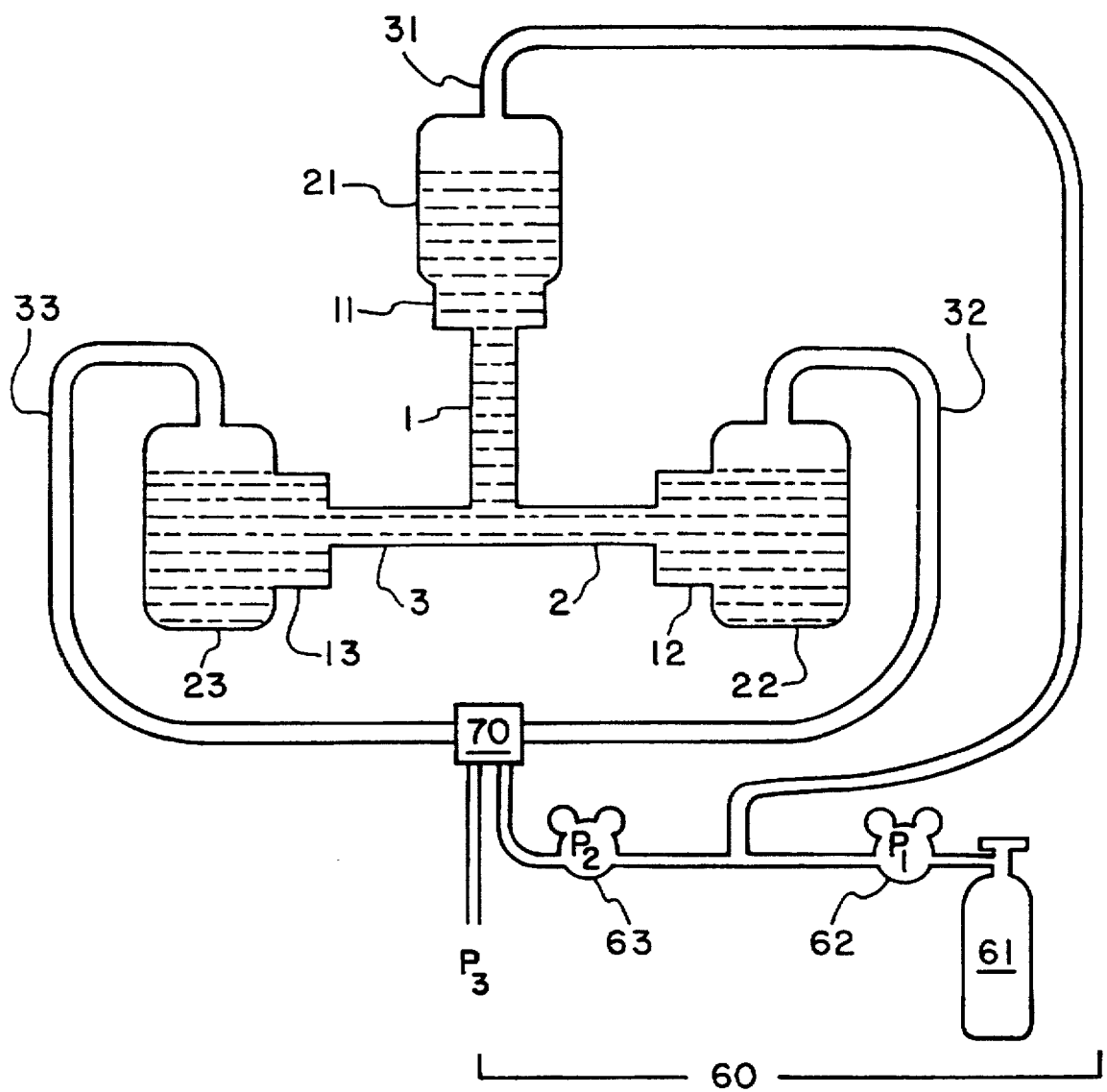

A minimum of one reservoir must have a switchable driving pressure. For greater versatility, more than one reservoir can have a switchable driving pressure. Each switchable driving pressure can have a separate switching means or a single switching means can be connected to more than one gas supply line, as illustrated in FIG. 3b. The pressure from gas cylinder 61 is controlled by regulator 62. Constant pressure $P_1$ is supplied to reservoir 21 via gas inlet line 31. The gas pressure is maintained at a lower pressure $P_2$ by regulator 63, which is connected to switch 70. Pressure $P_3$, which is atmospheric pressure in this embodiment, is also supplied to the switch. Switch 70 connects one supply line to each of gas inlet lines 32 and 33, and can switch to reverse the connections, such that $P_2'=P_3$ and $P_3'=P_2$. This embodiment of the pressure control and switching means is particularly suited for a microswitch having identical channel geometry for channels 2 and 3 so that a given driving pressure will produce the same junction pressure when applied to either channel.

Figure 4:
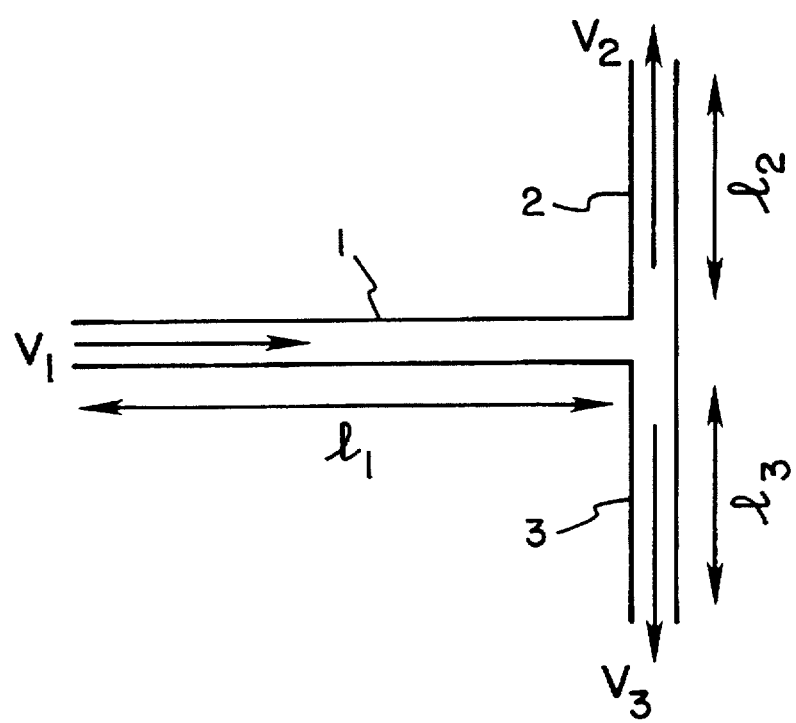
FIG. 4 shows the quantities used to calculate the required driving pressures.

The required driving pressures can be calculated from the channel geometries, as depicted in FIG. 4. In this embodiment channels 1, 2 and 3 are etched to the same depth and have the same width. The lengths of the channels are $l_1$, $l_2$ and $l_3$, and the liquid velocities in the channels are $v_1$, $v_2$ and $v_3$. When all the flow goes from channel 1 to channel 2, then $v_1=v_2$ and $v_3=0$. This is achieved by setting $P_1>P_2$ to create a pressure gradient along channels 1 and 2, and by setting $P_3$ equal to the pressure at the junction of the channels, $P_J$. The junction pressure $P_J$ is between $P_1$ and $P_2$. When $P_3=P_J$, since there is no pressure differential between the junction and the third reservoir, liquid does not flow along channel 3. The required pressure $P_3$ given in terms of the applied pressures $P_1$ and $P_2$ is $$P_3 = P_J = \frac{(P_1 - P_2)l_2}{l_1 + l_2} + P_2. \quad (2)$$

This expression can be derived by analogy to an electrical circuit of three resistors, where length, velocity and pressure are analogous to resistance, current and voltage, respectively. If the channels are of varying depths and widths, or include other features which affect conductance, the calculation is more complicated but straightforward to those skilled in the art.

For operating the switch with one inlet channel and two outlet channels, as described above, the driving pressures are switched between a first state having $P_1>P_2$, $P_3=P_J$ and a second state having $P_1'>P_3'$, $P_2'=P_J'$. To switch between two inlet channels having a common outlet channel, the driving pressures are switched between $P_2>P_1$, $P_3=P_J$ and $P_3'>P_1'$, $P_2'=P_J'$. To switch between flow from channel 1 to channel 2 and flow from channel 3 to channel 1, the driving pressures are switched between $P_1>P_2$, $P_3=P_J$ and $P_3'>P_1'$, $P_2'=P_J'$. In all cases there is a pressure differential between the flowing channels and the driving pressure behind the nonflowing (off) channel equals the junction pressure. There is a great range of driving pressures that can meet these conditions. The driving pressures are selected to provide the desired flow rates and to be compatible with the pressure control and switching means.

The pressure at the junction is not necessarily measured directly, but can be estimated as in Eq. 2. The term junction pressure as used herein refers to either the actual or calculable pressure at the junction. To stop flow in a channel the driving pressure at the corresponding reservoir is set approximately equal to the junction pressure. Depending on the particular switch geometry, the pressures need not be exactly equal to stop flow in the channel. Also, depending on the application in which the switch is used, some leakage may be tolerated in the switch, so the pressures only need to be equal within the range of tolerable leakage. For cases where the junction pressure is calculated rather than measured, the driving pressure may exactly equal the calculated junction pressure but only approximately equal the actual junction pressure. Empirically, when the flow is stopped in a channel, the driving pressure behind that channel must approximately equal the junction pressure.

The microswitch of this invention can further include means for measuring the driving pressures at one or more reservoir or means for measuring the pressure in one or more channel or at the junction of the channels. There can be active feedback between the pressure sensor and the pressure control means to maintain the desired pressure.

Figure 5:
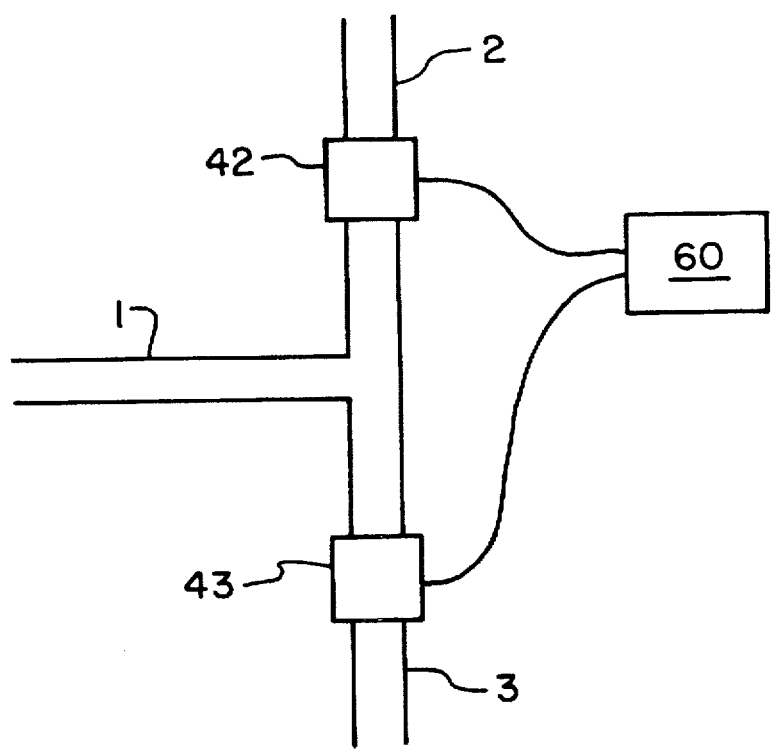
FIG. 5 shows flow sensors on the microswitch channels.

The flow in one or more channels can be measured directly with flow sensors on the channels, as shown in FIG. 5. Sensors 42 and 43 are positioned along channels 2 and 3, respectively. The sensors can feedback to pressure control means 60 to actively control the flow in the channels. The sensors used in this switch need not determine the exact flow rate; it is sufficient to use a null flow sensor to determine whether the liquid is flowing or stationary. In the embodiment of FIG. 3b, once the pressures have been tuned to stop flow in one output channel, switching means 70 can switch between the two output channels without further adjustment of the driving pressures, so a flow sensor is only required on one channel. In a system with active feedback control of the driving pressures, a fail safe mechanism can be included to indicate when the driving pressures have been increased beyond an expected range, suggesting a channel blockage.

Many liquid microflow sensors are known in the art (Shoji et al., J. Micromech Microeng. 4 (1994), 157–171). They can be based, for example, on thermotransfer, thermal time-of-flight or differential pressure. The flow can also be determined optically using a light source and a photodetector. In a preferred embodiment, fluorescent microspheres are added to the liquid as a flow tracer. The microspheres are optically excited and movement of the spheres is monitored by a photodetector, such as a human eye or an electronic photodetector. The spheres are made stationary in the off channel by manual or automatic adjustment of the driving pressures. Scattering of light from particles in the liquid can also be used to optically measure flow. The rate at which scattering or fluorescing particles pass the detector can be measured. For a null flow sensor the driving pressure can be adjusted until no particles pass the detector.

Figure 6:
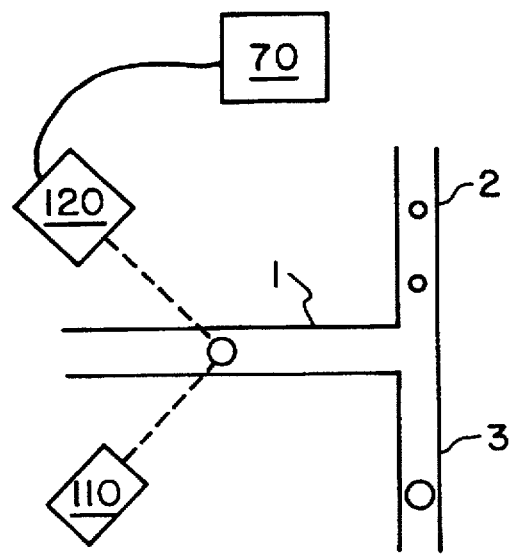
FIG. 6 is a flow cytometer using the microswitch to sort particles.

The microswitch of this invention can be used in a great number of microfluidic systems. FIG. 6 shows the switch used as a flow sorter in combination with a flow cytometer. The flow cytometer comprises light source 110 and photodetector 120. The photodetector can be positioned to detect small or large angle scattered light or fluorescence. A microfabricated flow cytometer is described in detail in U.S. patent application Ser. No. 08/534,515, filed Sep. 27, 1995, which is incorporated by reference herein in its entirety. In the present embodiment photodetector 120, which can incorporate signal analysis electronics, characterizes cells or other particles in the sample based on their fluorescence or scattering. The photodetector sends instructions to switching means 70, which then directs each particle to the appropriate outlet channel. This can be used to separate white and red blood cells, or to otherwise separate particles on the basis of size, shape or fluorescence characteristics. For a flow cytometer having a flow rate on the order of $10^3$ particles per second, the switching time must be in the millisecond range. This speed can be provided by the microswitch of this invention.

Figures 7A, 7B:
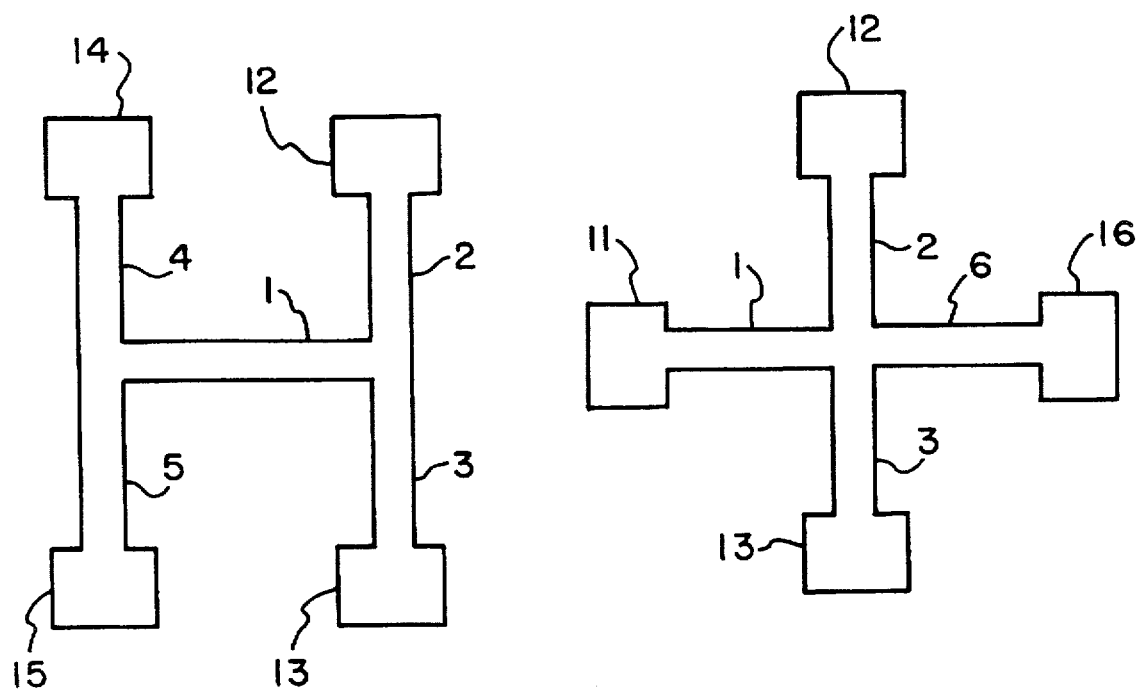
FIGS. 7a–b, shows microswitches having (a) two three-channel junctions and (b) a four-channel junction.

More than three channels can be controlled with the microswitches of this invention. In FIG. 7a, a fourth channel, 4, with port 14 joins channel one to form a second junction. This divides channel one into sections 1 and 5, with port 15. This can also be thought of as replacing the single port to channel 1 by the combination of channels 4 and 5, and ports 14 and 15. By controlling the driving pressures behind each channel, flow into channel 1 can be switched between channels 4 and 5 and the flow out of channel 1 can be switched between channels 2 and 3. The two junction switch can also operate with other flow patterns between the channels. The driving pressures can be switched so that any of the channels is on an inlet and any channel is an outlet.

Four channels join in a single junction in FIG. 7b. Flow from channel 1 can be outlet to any of channels 2, 3 or 6 by adjusting the driving pressures. For flow from channel 1 to channel 2, for example, the driving pressures are set so that $P_1 > P_2$ and $P_3 = P_6 = P_j$. The switch can be operated in a number of modes, with any of the channels being inlets and any being outlets. FIGS. 7a–b illustrate two switches having more than three channels. Many other networks of channels can also be controlled with the microswitches of this invention. Additional channels can join and branch to form additional junctions, and each junction can accommodate more than three channels.

A microswitch of this invention was fabricated and operated as described below. Channels as shown in FIGS. 1–2 were micromachined in a silicon (100) wafer using standard photolithography techniques to pattern the channels and connection ports. Ethylene-diamine, pyrocatechol (EDP) was used for a two-step etch. A Pyrex 7740 coverplate was anodically bonded to the face of the silicon to provide a closed liquid system. Liquid connections were made on the backside of the silicon. The channels were 10 µm deep. The combined length of channel one with either channel two or three was 1 cm. Channel one was 10 µm in diameter and channels two and three were each 30 µm in diameter.

A 0.01% solution of 0.5 µm diameter fluorescing beads was used to visualize the flow. These polystyrene beads contain a dye which fluoresces in the red when excited by light around 550 nm. They are essentially neutrally buoyant and provide an excellent means of flow visualization. These beads were imaged on an inverted Zeiss microscope with a Dage silicon intensified target (SIT) video-rate camera. The video data was recorded on S-VHS video tape.

Because of the short channel length (1 cm) and tiny flow rates (10 nl/sec), only modest pressures were required to drive the liquid. Under low Reynolds number conditions, Poiseuille's law, $P/l = 128 \eta v/d^4$, determines the pressure drop of a fluid of viscosity $\eta$ flowing at a maximum velocity $v$ in a cylindrical channel with diameter d and length l. Pressures of a few PSI were used to achieve flow velocities of a few mm/sec. The highest Reynolds numbers reached were $\sim 10^{-1}$.

The pressure control and switching means were as shown in FIG. 3b using a compressed nitrogen cylinder. The pressure $P_1$ at port 1 was first fixed at 1 psi above atmospheric pressure and then the pressure at $P_2$ was adjusted so that the flow rate in channel two was zero, which occurred at 0.5 psi. All flow was from channel one to channel three. Pressure $P_3$ was vented to atmosphere. Switching means 70 was a 5–3 valve, which allowed rapid switching. By actuating this external valve, the pressures behind channel two and channel three were rapidly switched. This forced the fluid to rapidly switch from flowing down channel three to channel two. Because the geometries of channels two and three were identical, the pressures could be simply switched between them.

Figure 8:
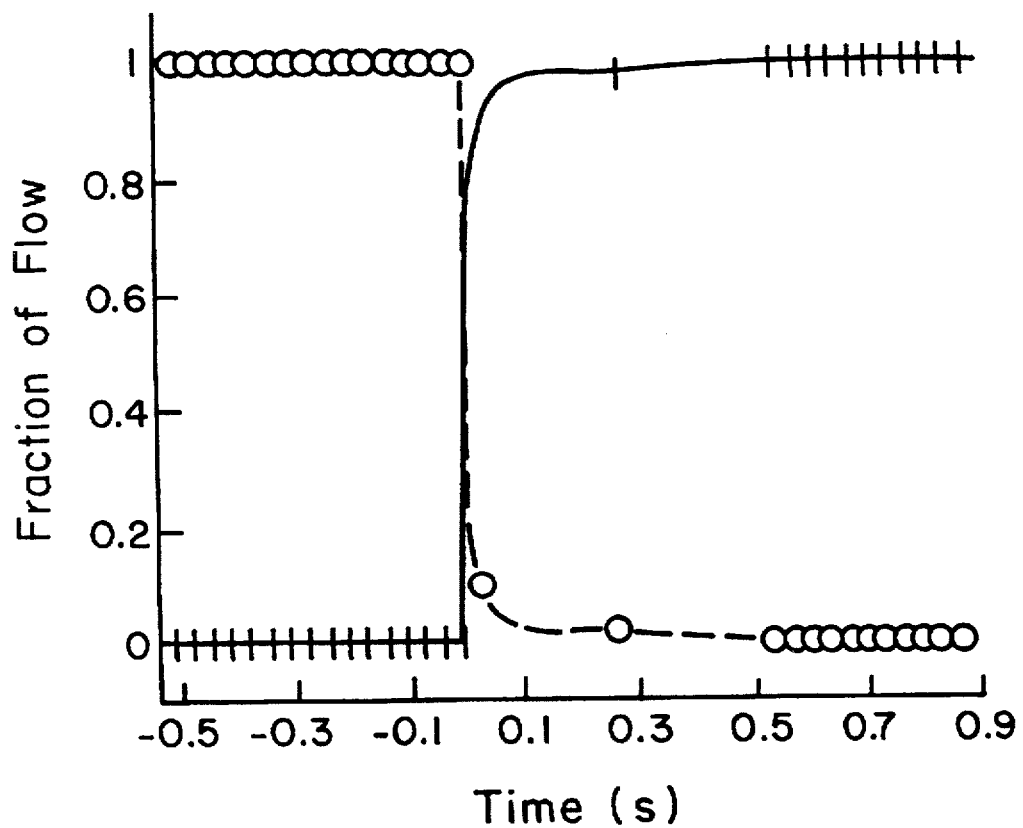
FIG. 8 is measured flow of a three-channel microswitch as it is switched from a first to a second output channel.

Video images of the fluorescent beads were analyzed frame-by-frame and the relative flow rates in the two channels were recorded, as shown in FIG. 8. Flow to one channel is shown with circles, and the other channel is shown with hatches. The switching was completed within 100 ms. This switching time is limited by the pressure control and switching system, not by the fluid dynamics of the switch. The leakage to the off channel was <1%.

The microswitch of this invention has been illustrated above with a few specific embodiments. As will be apparent to those skilled in the art, many other embodiments and applications of the switch can be constructed. The switch can be fabricated with channels from materials other than silicon, such as glass or plastic. The channel dimensions, shapes and orientations can be varied. Multiple junctions can be employed in a network. The network can be three dimensional rather than two dimensional. The pressure control and switching means can have different configurations and operating conditions from those illustrated. Like the flow channels, they can be microfabricated. Faster pressure switches can be used, such as piezoelectric switches. The switch can be combined with other liquid handling, treating and analyzing apparatus, for example in a network including reagent, flush and waste reservoirs connected to a reaction chamber, other microfabricated elements such as valves and pumps, or chemical, electrical and optical analysis regions. These and other variations fall within the spirit and scope of this invention.

I claim:

1. A liquid microswitch comprising:
    a first, a second and a third microchannel, each having a junction end and a port end, said first, second and third microchannels joined at said junction ends to form a first junction;
    a first, a second and a third liquid reservoir, attached to the port ends of said first, second and third microchannels, respectively;
    a pressure control means for applying a first driving pressure, $P_1$, a second driving pressure, $P_2$, and a third driving pressure, $P_3$, to said first, second and third liquid reservoirs, respectively, wherein, in a first switching state, $P_1$ is greater than or less than $P_2$, and $P_3$ is approximately equal to $P_j$, the pressure at said first junction; and
    a switching means, connected to said pressure control means, for switching said first, second or third driving pressure to a second switching state, wherein $P_1'$ is greater than or less than $P_3'$, and $P_2'$ is approximately equal to $P_j'$.

2. The microswitch of claim 1 wherein in said first switching state $P_1 > P_2$ and in said second switching state $P_1' > P_3'$.

3. The microswitch of claim 1 wherein in said first switching state $P_1 < P_2$ and in said second switching state $P_1' < P_3'$.

4. The microswitch of claim 1 wherein in said first switching state $P_1 > P_2$ and in said second switching state $P_1' < P_3'$.

5. The microswitch of claim 1 wherein said switching means simultaneously switches two of said driving pressures.

6. The microswitch of claim 5 wherein said switching means simultaneously switches all three of said driving pressures.

7. The microswitch of claim 5 wherein said driving pressures are switched so that $P_2'=P_3$ and $P_3'=P_2$.

8. The microswitch of claim 7 wherein the channel dimensions of said second and third channels are equal.

9. The microswitch of claim 1 further including a flow sensor on one of said microchannels.

10. The microswitch of claim 9 further including a second flow sensor on a second of said microchannels.

11. The microswitch of claim 10 further including a third flow sensor on a third of said microchannels.

12. The microswitch of claim 9 wherein said flow sensor is an optical flow sensor.

13. The microswitch of claim 12 wherein said optical flow sensor comprises a light source and a photodetector.

14. The microswitch of claim 13 wherein said optical flow sensor is adapted to sensing fluorescence from particles.

15. The microswitch of claim 13 wherein said optical flow sensor is adapted to sensing light scattering from particles.

16. The microswitch of claim 9 wherein said flow sensor is a null flow sensor.

17. The microswitch of claim 9 wherein said flow sensor is coupled to said pressure control means.

18. The microswitch of claim 1 further including a pressure sensor positioned on one of said microchannels or at said junction.

19. The microswitch of claim 18 wherein said pressure sensor is coupled to said pressure control means.

20. The microswitch of claim 1 wherein the characteristic dimension of said microchannels is between about 0.5 μm and 1 mm.

21. The microswitch of claim 20 wherein the characteristic dimension of said microchannels is between about 5μ and 100 μm.

22. The microswitch of claim 1 wherein said microchannels are formed in a silicon wafer.

23. The microswitch of claim 22 wherein said silicon wafer contains an additional fluidic, optical, electronic or mechanical element.

24. The microswitch of claim 22 wherein said microchannels are formed in the surface of a silicon wafer and wherein said surface is sealed by a transparent coverplate.

25. The microswitch of claim 22 wherein said microchannels are formed in the surface of a silicon wafer and wherein said surface is sealed by a coverplate containing an additional fluidic, optical, electronic or mechanical element.

26. The microswitch of claim 22 wherein said first junction is T-shaped.

27. The microswitch of claim 1 wherein said first junction is Y-shaped.

28. The microswitch of claim 1 wherein the switching time of said microswitch is less than 1 s.

29. The microswitch of claim 28 wherein said switching time is less than 10 ms.

30. The microswitch of claim 29 wherein said switching time is less than 100 μs.

31. The microswitch of claim 1 further comprising a fourth microchannel having a junction end and a port end, said junction end joining said first microchannel to form a second junction.

32. The microswitch of claim 31 further comprising a fourth liquid reservoir attached to the port end of said fourth microchannel, and wherein said pressure control means further applies a fourth driving pressure, $P_4$, to said fourth liquid reservoir.

33. The microswitch of claim 1 further comprising a fourth microchannel having a junction end and a port end, said junction end joining said first junction.

34. The microswitch of claim 33 further comprising a fourth liquid reservoir attached to the port end of said fourth microchannel, and wherein said pressure control means further applies a fourth driving pressure, $P_4$, to said fourth liquid reservoir.

35. The microswitch of claim 34 wherein, in said first switching state, $P_4$ is approximately equal to $P_J$.

36. The microswitch of claim 1 further including a flow cytometer optically coupled with said first microchannel.

37. The microswitch of claim 36 wherein said flow cytometer comprises a light source and a photodetector.

38. The microswitch of claim 37 wherein said photodetector is coupled to said switching means.

39. A method of switching the liquid flow route at the junction of first, second and third microchannels, said method comprising the steps of:

applying a first driving pressure, $P_1$, a second driving pressure, $P_2$, and a third driving pressure, $P_3$, behind said first, second and third microchannels, respectively, wherein $P_1$ is greater than or less than $P_2$, and $P_3$ is approximately equal to $P_J$, the pressure at said junction; and switching said first, second or third driving pressure to a second switching state, wherein $P_1'$ is greater than or less than $P_3'$, and $P_2'$ is approximately equal to $P_J'$.

* * * * *